United States Patent [19]

Wu

[11] Patent Number: 5,422,172
[45] Date of Patent: Jun. 6, 1995

[54] ELASTIC LAMINATED SHEET OF AN INCREMENTALLY STRETCHED NONWOVEN FIBROUS WEB AND ELASTOMERIC FILM AND METHOD

[75] Inventor: Pai-Chuan Wu, Cincinnati, Ohio

[73] Assignee: Clopay Plastic Products Company, Inc., Cincinnati, Ohio

[21] Appl. No.: 104,791

[22] Filed: Aug. 11, 1993

[51] Int. Cl.6 .......................... D03D 17/00; B32B 7/12
[52] U.S. Cl. ..................................... 428/230; 428/231; 428/286; 428/287
[58] Field of Search ................ 428/230, 231, 286, 287

[56] References Cited

U.S. PATENT DOCUMENTS

| | | | |
|---|---|---|---|
| 2,714,571 | 8/1955 | Irion et al. | 154/139 |
| 3,058,868 | 10/1962 | Palatine, III | 156/153 |
| 3,622,422 | 11/1971 | Newmann | 156/306 |
| 3,868,729 | 3/1975 | Lynam | 428/230 X |
| 4,153,664 | 5/1979 | Sabee | 264/289 |
| 4,366,814 | 1/1983 | Riedel | 428/230 X |
| 4,379,197 | 4/1983 | Cipriani et al. | 428/220 |
| 4,517,714 | 5/1985 | Sneed et al. | 28/103 |
| 4,522,203 | 6/1985 | Mays | 128/132 |
| 4,614,679 | 9/1986 | Farrington, Jr. | 428/138 |
| 4,692,368 | 9/1987 | Taylor et al. | 428/137 |
| 4,725,473 | 2/1988 | Gompel et al. | 428/156 |
| 4,753,840 | 6/1988 | Gompel | 428/171 |
| 4,761,324 | 8/1988 | Rautenberg et al. | 428/230 X |
| 5,035,941 | 7/1991 | Blackburn | 428/286 |
| 5,049,426 | 9/1991 | Kimura et al. | 428/230 X |
| 5,221,572 | 6/1993 | Meunier | 428/231 |

*Primary Examiner*—Daniel R. Zirker
*Attorney, Agent, or Firm*—Wood, Herron & Evans

[57] ABSTRACT

An elastic laminated sheet of an incrementally stretched nonwoven fibrous web and elastomeric film and method of making are disclosed. The elastic laminates are especially useful in diapers, surgical gowns, sheets, dressings, hygienic products and the like.

12 Claims, 3 Drawing Sheets

ELASTIC LAMINATED SHEET OF AN INCREMENTALLY STRETCHED NONWOVEN FIBROUS WEB AND ELASTOMERIC FILM AND METHOD

BACKGROUND OF THE INVENTION

Processes of bonding nonwoven fibrous webs to thermoplastic films have been known for some time. Additionally, methods for extrusion laminating thermoplastic films to unstretched nonwoven webs are well known in the art.

Relevant patents regarding extrusion lamination of unstretched nonwoven webs include U.S. Pat. Nos. 2,714,571; 3,058,863; 4,522,203; 4,614,679; 4,692,368; 4,753,840 and 5,035,941. The above '863 and '368 patents disclose stretching extruded polymeric films prior to laminating with unstretched nonwoven fibrous webs at pressure roller nips. The '203 and '941 patents are directed to co-extruding multiple polymeric films with unstretched nonwoven webs at pressure roller nips. The '840 patent discloses preforming nonwoven polymeric fiber materials prior to extrusion laminating with films to improve bonding between the nonwoven fibers and films. More specifically, the '840 patent discloses conventional embossing techniques to form densified and undensified areas in nonwoven base plies prior to extrusion lamination to improve bonding between nonwoven fibrous webs and films by means of the densified fiber areas. The '941 patent also teaches that unstretched nonwoven webs that are extrusion laminated to single ply polymeric films are susceptible to pinholes caused by fibers extending generally vertically from the plane of the fiber substrate and, accordingly, this patent discloses using multiple co-extruded film plies to prevent pinhole problems. Furthermore, methods for bonding loose nonwoven fibers to polymeric film are disclosed in U.S. Pat. Nos. 3,622,422; 4,379,192 and 4,725,473.

It has also been known to stretch nonwoven fibrous webs using intermeshing rollers to reduce basis weight and examples of patents in this area are U.S. Pat. Nos. 4,153,664 and 4,517,714. The '664 patent discloses a method of incremental cross direction (CD) or machine direction (MD) stretching nonwoven fibrous webs using a pair of interdigitating rollers to strengthen and soften nonwoven webs. The '664 patent also discloses an alternative embodiment wherein the nonwoven fibrous web is laminated to the thermoplastic film prior to intermesh stretching.

There is a continuing need for improved laminates of nonwoven fibrous substrates in plastic films that provide sufficient absorbency and softness. It would be very desirable to further improve the properties of such laminates and to expand their utilities in articles of clothing and other useful products. Improvements are also desirable in methods of producing such laminates on high speed production machinery.

SUMMARY OF THE INVENTION

This invention is directed to an elastic laminated sheet of a nonwoven fibrous web and an elastomeric film. The term "elastic" is used in the specification and claims as meaning stretchable under force and recoverable to its original or essentially original form upon release of that force. The fibrous web has a multitude of fibers extending outwardly from the laminated surface that are formed by incremental stretching of the laminated sheet along lines substantially uniformly across the laminated sheet and throughout its depth. The laminated elastomeric film is stretchable and recoverable to provide elasticity to the laminated sheet.

This invention also provides a method for producing the elastic laminate on high speed production machinery at line speeds of about 500 fpm. Thus, this invention provides for laminates of nonwoven fibrous substrates and elastomeric films that have sufficient absorbency and softness with new properties of stretchability and recoverability. The unique laminates and properties enable the laminated sheet to be used for many purposes including particularly articles of clothing where stretchability and recoverability are significant properties.

The elastic laminated sheet comprises a nonwoven fibrous web and an elastomeric film laminated to at least one web surface. The elastomeric film may be on one side of the nonwoven or between the nonwovens to form the elastic laminate. The laminate is incrementally stretched along lines substantially uniformly across its length and width and throughout its depth to form a stretchable and recoverable composite. Thus, stretched zones may be separated or bordered by unstretched zones in the laminate to provide elasticity to the laminate. Elasticity in the composite is mainly attributable to the elastic film. Under elongation or deformation forces, the laminate is stretchable and thus would conform, for example, to parts of the body when employed as a fabric in an article of clothing. Similarly, with the unique property of elastic recovery, the laminate will essentially return to its original state. Furthermore, it may be repeatedly subjected to stretching and recovery.

In a most preferred form, the method of this invention involves lamination by extrusion or adhesion of the nonwoven fibrous web to the elastomeric film. Preferably the method may be conducted on high speed production machinery on the order of about 500 fpm. It involves inline lamination and incremental stretching. More specifically, a nonwoven fibrous web is introduced into a nip of rollers for extrusion lamination with an elastomeric film. An elastomeric extrudate is extruded into the nip at a temperature above its softening point to form a film laminated to the fibrous web. The compressive force between the fibrous web and extrudate at the nip is controlled to bond one surface of the web to the film to form the laminate. As indicated above, the laminate or composite may also be formed by adhesively bonding the fibrous web to the elastomeric film. The thus formed laminate is then incrementally stretched along lines substantially uniformly across the laminate and throughout its depth to provide an elastic laminated sheet. By applying an incremental stretching force to the laminated sheet, both the web and the film are stretched. Upon removing the stretching force from the laminated sheet, the elastic film recovers its shape and fibers of the web are thereby caused to extend outwardly from the bonded web surface to give loft to the laminated sheet.

Other benefits, advantages and objectives of this invention will be further understood with reference to the following detailed description.

DETAILED DESCRIPTION

It is a primary objective of this invention to produce an elastic laminated sheet of a nonwoven fibrous web and an elastomeric film on high speed production machinery to produce recoverable and stretchable laminates. It is a further objective to produce such laminates having satisfactory bond strengths while maintaining the appearance of fabric and soft feel. As developed above, these and other objectives are achieved in preferred form of the invention by first incrementally stretching a laminated sheet of nonwoven fibrous web and elastomeric film along lines substantially uniformly across the laminate and throughout its depth. It has been found, by incrementally stretching the laminate, that an elastic sheet material is produced where the fibrous web is bonded to the elastomeric film, yet the sheet is stretchable and recoverable to essentially its original state. Furthermore, it has been found that such a laminated composite may be made by extrusion and stretching inline in order to achieve production speeds on the order of about 500 fpm. The elastic laminate in one form is characterized by being impervious to the passage of fluid by virtue of the elastomeric film while maintaining a soft feel on the fibrous web surface of the laminate. Alternatively, various degrees of vapor or air permeability may be achieved in the laminate or composite by providing mechanical microvoids, for instance. In a preferred form, the elastic laminate of this invention has the desirable feature of soft feel to achieve utility in a number of applications including diapers, pants, surgical gowns, sheets, dressings, hygienic products and the like.

A. Materials for the Laminate

The elastomeric film preferably is of the polyolefin type that is processable into a film for direct lamination by melt extrusion onto the fibrous web in one embodiment. Suitable elastomeric polymers may also be biodegradable or environmentally degradable. Suitable elastomeric polymers for the film include poly(ethylene-butene), poly(ethylene-hexene), poly(ethylene-octene), poly(ethylene-propylene),poly(styrene-butadiene-styrene), poly(styrene-isoprene-styrene), poly(styrene-ethylene-butylene-styrene), poly(ester-ether), poly(ether-amide), poly(ethylene-vinylacetate), poly(ethylene-methylacrylate), poly(ethylene-acrylic acid), poly(ethylene butylacrylate), polyurethane, poly(ethylene-propylene-diene), ethylene-propylene rubber. A new class of rubber-like polymers may also be employed and they are generally referred to herein as polyolefins produced from single-cite catalysts. The most preferred catalysts are known in the art as metallocene catalysts whereby ethylene, propylene, styrene and other olefins may be polymerized with butene, hexene, octene, etc., to provide elastomers suitable for use in accordance with the principles of this invention, such as poly(ethylene-butene), poly(ethylene-hexene), poly(ethylene-octene), poly(ethylene-propylene) and/or polyolefin terpolymers thereof.

The nonwoven fibrous web may comprise fibers of polyethylene, polypropylene, polyesters, rayon, cellulose, nylon, and blends of such fibers. A number of definitions have been proposed for nonwoven fibrous webs. The fibers are usually staple fibers or continuous filaments. As used herein "nonwoven fibrous web" is used in its generic sense to define a generally planar structure that is relatively flat, flexible and porous, and is composed of staple fibers or continuous filaments. For a detailed description of nonwovens, see "Nonwoven Fabric Primer and Reference Sampler" by E. A. Vaughn, Association of the Nonwoven Fabrics Industry, 3d Edition (1992). The nonwovens may be carded, spun bonded, wet laid, air laid and melt blown as such products are well known in the trade.

In a preferred form, the elastic laminated sheet employs an elastomeric film having a gauge or a thickness between about 0.25 and 10 mls and, depending upon use, the film thickness will vary and, most preferably, in disposable applications is the order of about 0.25 to 2 mils in thickness. The nonwoven fibrous webs of the laminated sheet normally have a weight of about 10 grams per square yard to 60 grams per square yard preferably about 20 to about 40 grams per square yard. When employing adhesive lamination, adhesives such as hot melt adhesive, water base adhesive or solid base adhesive may be used. The composite or laminate can be incrementally stretched in the cross direction (CD) to form a CD stretchable and recoverable composite. Furthermore, CD stretching may be followed by stretching in the machine direction (MD) to form a composite which is stretchable and recoverable in both CD and MD directions. As indicated above, the composite or laminate may be used in many different applications such as baby diapers, baby training pants, catamenial pads and garments, and the like where stretchable and recoverable properties, as well as fluid barrier properties are needed.

B. Stretchers For the Laminates

A number of different stretchers and techniques may be employed to stretch the starting or original laminate of a nonwoven fibrous web and elastomeric film. Laminates of nonwoven carded fibrous webs of staple fibers or nonwoven spun-bonded fibrous webs may be stretched with the stretchers and techniques described as follows:

1. Diagonal Intermeshing Stretcher

The diagonal intermeshing stretcher consists of a pair of left hand and right hand helical gear-like elements on parallel shafts. The shafts are disposed between two machine side plates, the lower shaft being located in fixed bearings and the upper shaft being located in bearings in vertically slidable members. The slidable members are adjustable in the vertical direction by wedge shaped elements operable by adjusting screws. Screwing the wedges out or in will move the vertically slidable member respectively down or up to further engage or disengage the gear-like teeth of the upper intermeshing roll with the lower intermeshing roll. Micrometers mounted to the side frames are operable to indicate the depth of engagement of the teeth of the intermeshing roll.

Air cylinders are employed to hold the slidable members in their lower engaged position firmly against the adjusting wedges to oppose the upward force exerted by the material being stretched. These cylinders may also be retracted to disengage the upper and lower intermeshing rolls from each other for purposes of threading material through the intermeshing equipment or in conjunction with a safety circuit which would open all the machine nip points when activated.

A drive means is typically utilized to drive the stationery intermeshing roll. If the upper intermeshing roll is to be disengageable for purposes of machine threading or safety, it is preferable to use an antibacklash gearing arrangement between the upper and lower intermeshing rolls to assure that upon reengagement the teeth of one intermeshing roll always fall between the teeth of the other intermeshing roll and potentially damaging physical contact between addendums of intermeshing teeth is avoided. If the intermeshing rolls are to remain in constant engagement, the upper intermeshing roll typically need not be driven. Drive may be accomplished by the driven intermeshing roll through the material being stretched.

The intermeshing rolls closely resemble fine pitch helical gears. In the preferred embodiment, the rolls have 5.935" diameter, 45° helix angle, a 0.100" normal pitch, 30 diametral pitch, 14½° pressure angle, and are basically a long addendum topped gear. This produces a narrow, deep tooth profile which allows up to about 0.090" of intermeshing engagement and about 0.005" clearance on the sides of the tooth for material thickness. The teeth are not designed to transmit rotational torque and do not contact metal-to-metal in normal intermeshing stretching operation.

2. Cross Direction Intermeshing Stretcher

The CD intermeshing stretching equipment is identical to the diagonal intermeshing stretcher with differences in the design of the intermeshing rolls and other minor areas noted below. Since the CD intermeshing elements are capable of large engagement depths, it is important that the equipment incorporate a means of causing the shafts of the two intermeshing rolls to remain parallel when the top shaft is raising or lowering. This is necessary to assure that the teeth of one intermeshing roll always fall between the teeth of the other intermeshing roll and potentially damaging physical contact between intermeshing teeth is avoided. This parallel motion is assured by a rack and gear arrangement wherein a stationary gear rack is attached to each side frame in juxtaposition to the vertically slidable members. A shaft traverses the side frames and operates in a bearing in each of the vertically slidable members. A gear resides on each end of this shaft and operates in engagement with the racks to produce the desired parallel motion.

The drive for the CD intermeshing stretcher must operate both upper and lower intermeshing rolls except in the case of intermeshing stretching of materials with a relatively high coefficient of friction. The drive need not be antibacklash, however, because a small amount of machine direction misalignment or drive slippage will cause no problem. The reason for this will become evident with a description of the CD intermeshing elements.

The CD intermeshing elements are machined from solid material but can best be described as an alternating stack of two different diameter disks. In the preferred embodiment, the intermeshing disks would be 6" in diameter, 0.031" thick, and have a full radius on their edge. The spacer disks separating the intermeshing disks would be 5½" in diameter and 0.069" in thickness. Two rolls of this configuration would be able to be intermeshed up to 0.231" leaving 0.019" clearance for material on all sides. As with the diagonal intermeshing stretcher, this CD intermeshing element configuration would have a 0.100" pitch.

3. Machine Direction Intermeshing Stretcher

The MD intermeshing stretching equipment is identical to the diagonal intermeshing stretch except for the design of the intermeshing rolls. The MD intermeshing rolls closely resemble fine pitch spur gears. In the preferred embodiment, the rolls have a 5.933" diameter, 0.100" pitch, 30 Diametral pitch, 14½° pressure angle, and are basically a long addendum, topped gear. A second pass was taken on these rolls with the gear hob offset 0.010" to provide a narrowed tooth with more clearance. With about 0.090" of engagement, this configuration will have about 0.010" clearance on the sides for material thickness.

4. Incremental Stretching Technique

The above described diagonal, CD or MD intermeshing stretchers may be employed to produce the incrementally stretched laminate of nonwoven fibrous web and elastomeric film of this invention. The stretching operation is usually employed on an extrusion laminate of a nonwoven fibrous web of staple fibers or spunbonded filaments and elastomeric film. In one of the unique aspects of this invention an elastic laminate of a nonwoven fibrous web of spun-bonded filaments may be incrementally stretched to provide a very soft fibrous finish to the laminate that looks like carded fibers with superior bond strengths. The laminate of woven fibrous web and elastomeric film is incrementally stretched using, for instance, the CD intermeshing stretcher with one pass through the stretcher with a depth of roller engagement at about 0.090 inch to 0.120 inch at speeds from about 500 fpm to 1000 fpm or faster. The results of such CD incremental or intermesh stretching produces laminates or composites that have excellent stretchability and recoverability and yet provide superior bond strengths and soft fibrous textures.

DETAILED EXAMPLES OF THE INVENTION

The following examples illustrate the elastic laminates of this invention and methods of making them. In light of these examples and this further detailed description, it is apparent to a person of ordinary skill in the art that variations thereof may be made without departing from the scope of this invention.

The invention is further understood with reference to the drawings in which.

Comparative Examples I-1 and II-2

Extrusion lamination of low density polyethylene (LDPE) film to a nonwoven fibrous web was made for direct comparison with an elastic extrusion laminate that was incrementally stretched according to this invention.

I-1. Extrusion Laminate of Nonwoven Fibrous Web and Thermoplastic Film (Without Incremental Stretching)

Figure 1:
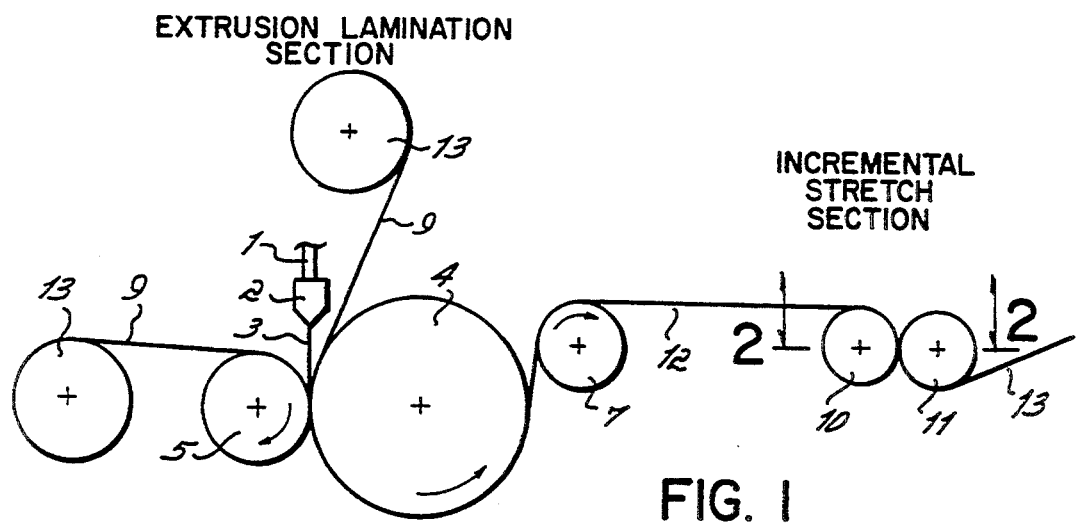
FIG. 1 is a schematic of an inline extrusion lamination and incremental stretching apparatus for making the laminate of this invention.
Figure 5:
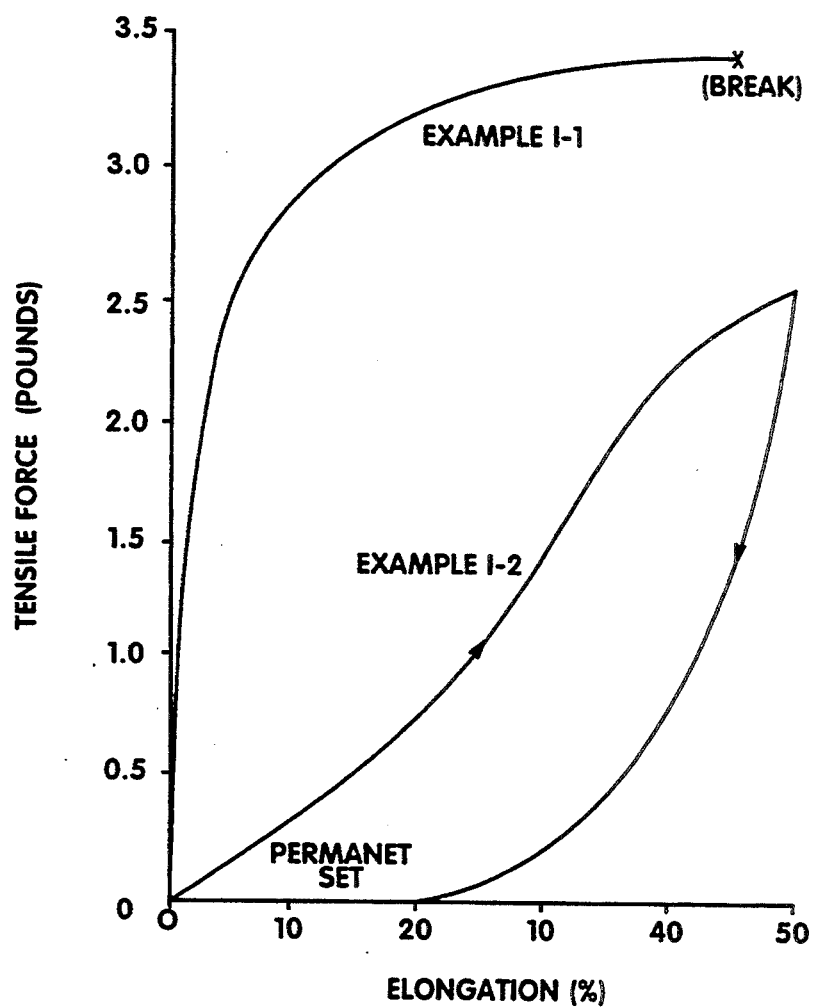
FIG. 5 is a graph demonstrating the elongation properties of comparative examples.

Two carded polypropylene nonwoven fibrous webs of 26 grams/yd$^2$ weight were laminated by extrusion of a LDPE thermoplastic film with a density of 0.914 g/cc at one mil between the webs according to the comparative extrusion lamination technique as shown in the extrusion lamination section of FIG. 1. As shown schematically in FIG. 1, the incoming webs 9,9 from rollers 13, 13 were introduced into the nip of a rubber roll 5 and a metal roll 4. The LDPE film 3 from extruder 1 was extruded through die 2 into the nip while the two carded fibrous webs 9,9 were introduced. Typically, at speeds over 500 fpm in this extrusion lamination section, the polyethylene film 3 on the order of about 0.25 to 10 mils in thickness is laminated at melt temperatures on the order of about 500°-625° F. to form the laminate 12 which is taken off at roller 7. The compressive force at the nip is controlled such that the webs are bonded to the polyolefin film to avoid pinholing and preserve the fibrous feel on the fiber surfaces of the laminate 12. Pressures on the order of about 10 to 80 psi are sufficient to achieve satisfactory bond for fibrous webs of about 10 to 60 grams/yd². In this example, the laminate is tested for its stretchability using an Instron Tensile Tester. A one inch strip cut along its cross machine direction (CD) is stretched at 20"/min. This composite breaks at 45% elongation with an ultimate tensile strength (broken strength) of 3.4 pounds per inch. This composite is not a stretchable and recoverable composite upon stretching and releasing of the stretch force. This is demonstrated in FIG. 5, (Comparative Example I-1).

Figure 2:
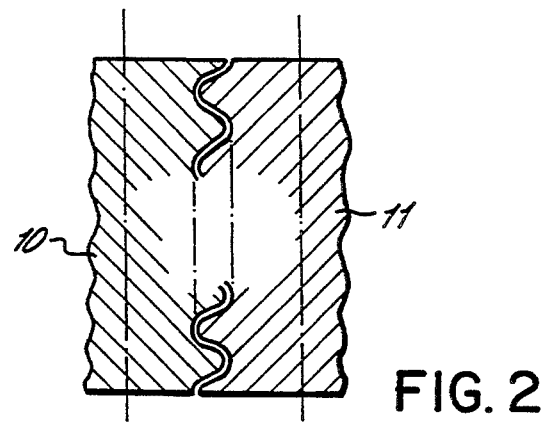
FIG. 2 is a cross sectional view taken along the line 2—2 of FIG. 1 illustrating the intermeshing rollers in diagrammatic form.

I-2. Extrusion Laminate of Nonwoven Fibrous Web and Thermoplastic Film With Incremental Stretching When the Composite of Comparative Example I-1 is incrementally stretched with reference to the incremental stretched section Of FIG. 1, the composite can then be stretched to more than 50% elongation. The stretching operation is schematically shown where the incoming web 12 was passed through the CD stretcher rollers 10 and 11 at a depth of roller engagement at about 0.100 inch and at about 500 fpm. The intermeshing rollers 10 and 11 are diagrammatically shown in FIG. 2 to illustrate the uniform stretching along lines across the laminate and through the depth of the laminate. The elastic property of the modified composite is then tested according to its stress (tensile force) and strain (elongation) by using an Instron Tensile Tester (see FIG. 5, Example I-2). The permanent set of this modified composite when stretched to 50% is 20% (see FIG. 5, Example I-2). "Permanent set" means the final unrecoverable dimension of the composite after being stretched. This non-elastic laminate is not a satisfactory stretchable and recoverable composite.

Example II

Elastic Laminate of Incrementally Stretched Nonwoven Fibrous Web and Elastomeric Film.

In this Example the same procedures are followed as for Example I, except the plastic used in extrusion lamination was DOW Chemical's elastomeric incite resin XU 51800.51 with a density of 0.870 grams per cubic centimeter. This new elastomeric resin is manufactured by using ethylene and octene comonomer with a new metallocene catalyst.

Figure 6:
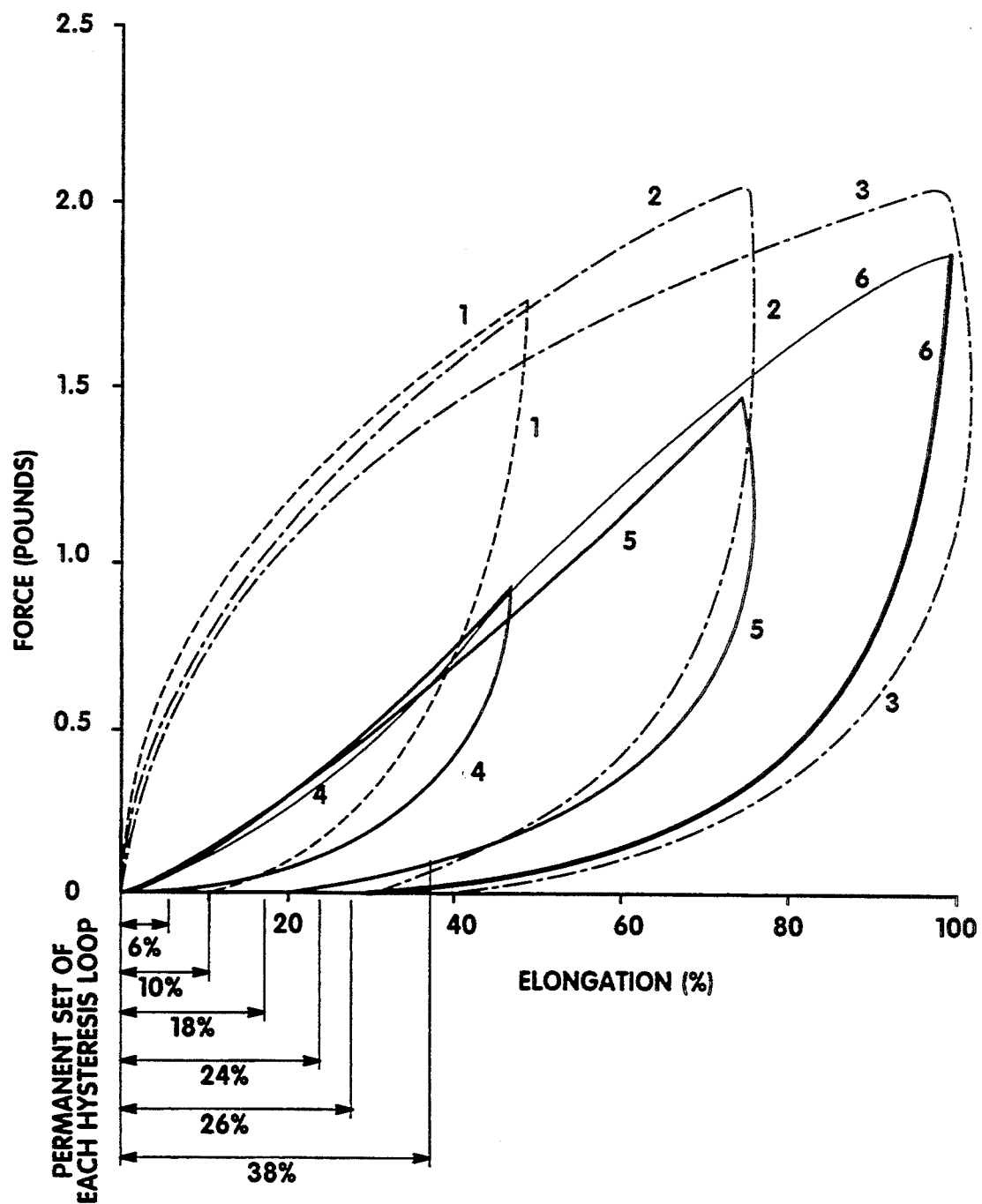
FIG. 6 is a graph demonstrating the elongation properties of elastic laminated sheets of this invention for comparison with comparative extrusion laminated composites.

The elastic laminate made in this Example, when CD incrementally stretched using an engagement of 0.100" is soft, stretchable and recoverable when compared to the laminate made according to Example I-1, except having a density of 0.870 g/cc. Table 1 and FIG. 6 show the detailed differences. The permanent set of the Example I-1 when stretched to 50% (FIG. 6, dotted curve 1), 75% (FIG. 6, dotted curve 2)), and 100% (FIG. 6, dotted curve 3) are 10%, 26% and 38%, respectively.

However the laminate becomes much softer and elastic according to this invention under less force when stretched to 50% (FIG. 6, solid curve 4), 75% (FIG. 6, solid curve 5) and 100% (FIG. 6, solid curve 6) are 6%, 18% and 24%, respectively. In its most preferred form, the permanent set of the laminate is no more than about 10% of its original dimension after first stretching to about 50% of its original shape.

The force required to stretch the laminate of Example II according to this invention is less than the comparative laminate (see Table 1). The recovery after releasing the force upon stretching is higher (or the permanent set is lower) with the laminate of this invention when compared to the comparative laminate. The product according to this invention will be suitable for diaper application such as the training pant or elastic waist and leg where the recoverable elastic sheet is needed.

Figure 3:
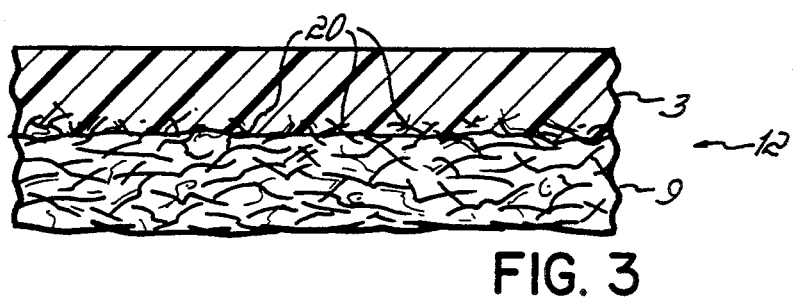
FIG. 3 is a magnified diagrammatic sketch in cross-section of a nonwoven fibrous web laminated to the elastomeric film before stretching.
Figure 4:
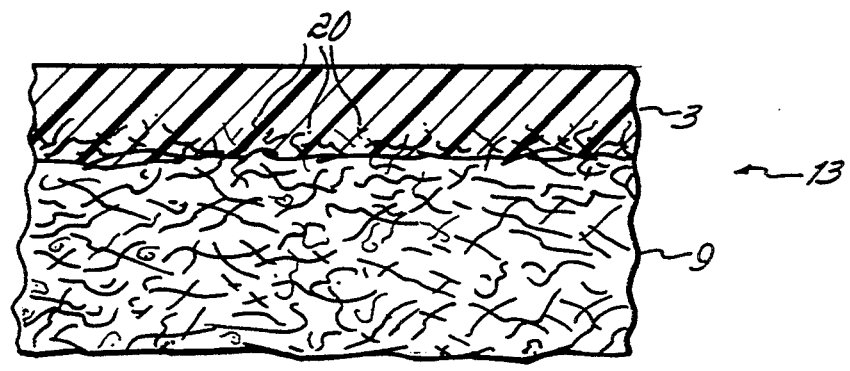
FIG. 4 is a magnified diagrammatic sketch of the laminate of FIG. 3 after incremental stretching to provide a composite where the fibers of the web are caused to extend outwardly from the surface to give high loft to the laminated sheet that is stretchable and recoverable according to the principles of this invention.

The high loft of the stretched elastic laminate is diagrammatically shown (FIG. 4) with reference to one side of the laminate before stretching (FIG. 3). The elastomeric film 3 is bonded to the surface fibers 20 of the web 9 in the extrusion lamination section of FIG. 1. To produce a laminate 12 where only one side is diagrammatically shown in FIG. 3. After incremental stretching, the fibers of the web 9 are caused to extend outwardly and provide a high loft of fibers to the laminate 13 as diagrammatically shown on one side in FIG. 4. The elastomeric film recovers its original or substantially original shape after stretching, whereas the web after stretching will increase in thickness and softness. This is one of the unique features of the laminate and method of this invention.

TABLE 1

|  | COMPARATIVE LAMINATE | | | LAMINATE OF THIS INVENTION | | |
| --- | --- | --- | --- | --- | --- | --- |
| TOTAL COMPOSITE WEIGHT (G/YD²) | 68 | | | 56 | | |
| BOND STRENGTH (G/IN) | TOTAL BOND | | | TOTAL BOND | | |
| STRETCHED TO AN ELONGATION SPECIFIED (%) | 50 | 75 | 100 | 50 | 75 | 100 |
| FORCE REQUIRED TO STRETCH TO THE SPECIFIED ELONGATION (LBS/IN) | 1.75 | 2.05 | 2.10 | 0.9 | 1.45 | 1.90 |
| PERMANENT SET AFTER THE STRETCHING TO THE SPECIFIED ELONGATION (%) | 10 | 26 | 38 | 6 | 18 | 24 |
| TENSILE STRENGTH AT 10% ELONGATION (LBS/IN) | 0.90 | 0.85 | 0.75 | 0.15 | 0.15 | 0.15 |

Example III

Two 34 grams per square yard of carded polypropylene nonwoven are extrusion laminated to an elastomeric film by using an elastomeric blend of styrene-butadiene-styrene block copolymer and EVA copolymer. The middle layer of the elastomeric film is at 2.0 mils. The composite so produced is then CD incrementally stretched by using an engagement of 0.100". The incrementally stretched laminate according to this invention becomes more stretchable and recoverable upon stretching and releasing of the force when compared to the comparative laminate of the above same elastomer composition without stretching. The force required to stretch the composite according to the invention is also lower. The results are shown in Table 2.

TABLE 2

|  | COMPARATIVE LAMINATE | | | LAMINATE OF THIS INVENTION | | |
| --- | --- | --- | --- | --- | --- | --- |
| Stretch to an elongation specified at (%) | 50 | 75 | 100 | 50 | 75 | 100 |
| Force required to stretch to the specified elongation (lbs/in) | 1.25 | 2.0 | 2.4 | 0.25 | 0.35 | 0.45 |
| Permanent set after stretching force is released (%) | 15 | 20 | 26 | 6 | 10 | 12 |

Example IV

A 41 grams per square yard carded polypropylene nonwoven is extrusion laminated by using an EPDM elastomer. This laminate is then CD incrementally stretched with a CD stretcher engagement of 0.100". The laminate becomes soft, stretchable and recoverable upon stretching and releasing of the stretch force and may be compared to the comparative laminate of same composition without incremental stretching as shown in the test results of Table 3.

TABLE 3

|  | COMPARATIVE LAMINATE | | | LAMINATE OF THIS INVENTION | | |
| --- | --- | --- | --- | --- | --- | --- |
| Stretch to an elongation specified at (%) | 50 | 75 | 100 | 50 | 75 | 100 |
| Force required to stretch to the specified elongation (lbs/in) | 1.2 | 1.5 | 1.6 | 0.5 | 0.7 | 0.9 |
| Permanent set after stretching force is released (%) | 10 | 18 | 24 | 9 | 15 | 17 |

Example V

A Scot carded polypropylene nonwoven with 30 grams per square yard and 2.0 mils of EPDM film is adhesively laminated by using an H. P. Fuller's EVA hot melt adhesive 2835. This laminated sheet is then incrementally stretched by using the CD stretcher at 0.100" engagement to produce a soft and elastic sheet. A comparative laminate of the same composition without incremental stretching was also run. Table 4 shows the test results.

TABLE 4

|  | COMPARATIVE LAMINATE | | | LAMINATE OF THIS INVENTION | | |
| --- | --- | --- | --- | --- | --- | --- |
| Stretch to an elongation specified at (%) | 50 | 75 | 100 | 50 | 75 | 100 |
| Force required to stretch to the specified elongation (lbs/in) | 2.2 | 2.6 | 2.8 | 0.9 | 1.5 | 2.0 |
| Permanent set after stretching force is released (%) | 8 | 19 | 25 | 6 | 14 | 18 |

Example VI

A DuPont sontara polyester fabric grade 8000 is extrusion laminated to DuPont polyester elastomer (Hytrel 8206) at 1.0 mil, The laminated sheet is then CD incrementally stretched by a CD incremental stretcher with an engagement of 0.100" to produce a soft, elastic, stretchable and recoverable composite. A comparative laminate of the same composition without incremental stretching was also run. Table 5 shows the test results.

TABLE 5

|  | COMPARATIVE LAMINATE | | | LAMINATE OF THIS INVENTION | | |
| --- | --- | --- | --- | --- | --- | --- |
| Stretch to an elongation specified at (%) | 50 | 75 | 100 | 50 | 75 | 100 |
| Force required to stretch to the specified elongation (lbs/in) | 1.6 | 2.2 | 3.0 | 0.7 | 0.8 | 1.1 |
| Permanent set after stretching force is released (%) | 18 | 32 | 42 | 8 | 17 | 23 |

Example VII

A DuPont Sontara polyester fabric grade 8000 is adhesive laminated to DuPont hytrel 8206 at 1.0 mil by using H. B. Fuller EVA hot melt adhesive 2835. The adhesive laminated sheet is then CD incrementally stretched by using a CD engagement of 0.08" followed with a MD stretching by using an engagement also of 0.08". The laminate is both a CD and MD stretchable and recoverable elastic composite. A comparative laminate of the same composition without incremental stretching was also run. The test results are shown on Table 6.

TABLE 6

|  | COMPARATIVE LAMINATE | | | | | | LAMINATE OF THIS INVENTION | | | | | |
| --- | --- | --- | --- | --- | --- | --- | --- | --- | --- | --- | --- | --- |
| Stretch to an elongation specified at (%) | 50% | | 75% | | 100% | | 50% | | 75% | | 100% | |
| Direction | MD | CD | MD | CD | MD | CD | MD | CD | MD | CD | MD | CD |
| Force required to stretch to the specified elongation (lbs/in) | NA* | 2.2 | NA* | 3.5 | NA* | 5.0 | 0.8 | 0.7 | 1.1 | 1.0 | 1.3 | 1.1 |
| Permanent set after stretching | NA* | 16 | NA* | 25 | NA* | 30 | 10 | 7 | 20 | 17 | 22 | 20 |

*NA - the material broke at 45% elongation

Example VIII

Exxon's Exact polymer type 4011 of ethylene and octene manufactured by using a Metallocene catalyst at a density of 0.885 g/cc extrusion laminated to DuPont's polyester sontara fabric grade 8000.

This extrusion laminated sheet is then CD incrementally stretched with an engagement of 0.090" followed with MD incremental stretching with an engagement of 0.065". The laminate is both CD and MD stretchable and recoverable. A comparative laminate of the same composition without incremental stretching was also run. Table 7 shows the test results.

TABLE 7

| | COMPARATIVE LAMINATE | | | | | | LAMINATE OF THIS INVENTION | | | | | |
|---|---|---|---|---|---|---|---|---|---|---|---|---|
| Stretch to an elongation specified at (%) | 50% | | 75% | | 100% | | 50% | | 75% | | 100% | |
| Direction | MD | CD | MD | CD | MD | CD | MD | CD | MD | CD | MD | CD |
| Force required to stretch to the specified elongation (lbs/in) | NA* | 1.35 | NA* | 1.75 | NA* | 2.40 | 0.75 | 0.75 | 1.05 | 0.9 | 1.25 | 1.05 |
| Permanent set after stretching | NA* | 15 | NA* | 34 | NA* | 47 | 10 | 10 | 20 | 20 | 26 | 30 |

*NA - the material broke at 45% elongation

The above data and experimental results demonstrate the unique stretchable and recoverable properties of the elastic laminated sheets of this invention. Other variations will be apparent to a person of skill in the art without departing from this invention.

What is claimed is:

1. An elastic laminated sheet of a nonwoven fibrous web and an elastomeric film comprising
   an elastomeric film and
   a nonwoven fibrous web laminated to a surface of said film to form said laminated sheet, said laminated sheet having a multitude of fibers extending outwardly from said laminated surface, said fibers being formed by incremental stretching of the laminated sheet along lines substantially uniformly across the laminated sheet and throughout its depth, said laminated sheet being stretchable and recoverable, having a permanent set after being stretched to 50% of its original shape of no more than about 10%.

2. The elastic laminated sheet of claim 1 formed by extrusion or adhesive lamination.

3. The elastic laminated sheet of claim 1 wherein said fibrous web comprises fibers selected from the group consisting of polypropylene, polyethylene, polyester, cellulose, rayon, nylon and blends of two or more of such fibers.

4. The elastic laminated sheet of claim 1 wherein the polymer of said elastomeric film is selected from the group consisting of poly(ethylene-butene), poly(ethylene-hexene), poly(ethylene-octene), poly(ethylene-propylene), poly(styrene-butadiene-styrene), poly(styrene-isoprene-styrene), poly(styrene-ethylene-butylene-styrene), poly(ester-ether), poly(ether-amide), poly(ethylene-vinylacetate), poly(ethylene-methylacrylate), poly(ethylene-acrylic acid), poly(ethylene butylacrylate), polyurethane, poly(ethylene-propylene-diene), and ethylene-propylene rubber.

5. The elastic laminated sheet of claim 1 wherein said film has a thickness on the order of about 0.25 to about 10 mils.

6. The elastic laminated sheet of claim 1 wherein said nonwoven fibrous web has a weight of about 10 grams/square yard to about 60 grams/square yard.

7. The elastic laminated sheet of claim 1 wherein said elastomeric film has a thickness on the order of about 0.25 to about 2 mils and the nonwoven fibrous web has a weight on the order of about 20 to about 40 grams/square yard.

8. The elastic laminated sheet of claim 1 incrementally stretched in a cross direction to form a stretchable and recoverable composite in said cross direction.

9. The elastic laminated sheet of claim 1 incrementally stretched in both its cross direction and longitudinal direction to form a stretchable and recoverable composite which is stretchable and recoverable in both said cross and longitudinal directions.

10. The elastic laminated sheet of claim 1 wherein said elastomeric film has opposite surfaces and a nonwoven fibrous web is laminated to both surfaces to provide said laminated sheet.

11. The elastic laminated sheet of claim 1 wherein the polymer of said elastomeric film is a polyolefin polymer produced by a reaction conducted in the presence of a single site catalyst.

12. The elastic laminated sheet of claim 11 wherein the polyolefin is derived from the polymerization of monomers selected from the group consisting of ethylene, propylene, styrene, butene, hexene and octene, and mixtures thereof.

* * * * *